(12) United States Patent
Zanne et al.

(10) Patent No.: US 9,095,686 B2
(45) Date of Patent: Aug. 4, 2015

(54) DEVICE FOR THE CONTROLLED TRANSLATIONAL DISPLACEMENT OF AN ELONGATE ELEMENT

(75) Inventors: Philippe Zanne, Roppenheim (FR); Florent Nageotte, Wettolsheim (FR); Michel De Mathelin, Strasbourg (FR)

(73) Assignees: UNIVERSITE DE STRASBOURG, Strasbourg (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 440 days.

(21) Appl. No.: 12/994,557

(22) PCT Filed: May 26, 2009

(86) PCT No.: PCT/FR2009/000609
§ 371 (c)(1),
(2), (4) Date: Apr. 5, 2011

(87) PCT Pub. No.: WO2009/153438
PCT Pub. Date: Dec. 23, 2009

(65) Prior Publication Data
US 2011/0184390 A1 Jul. 28, 2011

(30) Foreign Application Priority Data
May 26, 2008 (FR) ...................................... 08 53422

(51) Int. Cl.
*A61B 17/00* (2006.01)
*A61B 1/00* (2006.01)
(Continued)

(52) U.S. Cl.
CPC ...... *A61M 25/09041* (2013.01); *A61B 1/00133* (2013.01); *A61B 1/018* (2013.01);
(Continued)

(58) Field of Classification Search
CPC ............... A61B 19/22; A61B 19/2203; A61B 2019/2242; A61B 17/00; B21J 15/28; A41H 37/00; B31B 1/68

USPC ............................................... 606/1; 600/106
See application file for complete search history.

(56) References Cited

U.S. PATENT DOCUMENTS

| 3,470,876 A | 10/1969 | Barchilon |
| 4,873,965 A | 10/1989 | Danieli |

(Continued)

FOREIGN PATENT DOCUMENTS

| EP | 1 782 744 A2 | 5/2007 |
| EP | 1 857 041 A1 | 11/2007 |
| WO | 00/07500 A1 | 2/2000 |

OTHER PUBLICATIONS

International Search Report, dated Nov. 20, 2009, from corresponding PCT application.

*Primary Examiner* — Lynsey Crandall
*Assistant Examiner* — Sebastian X Lukjan
(74) *Attorney, Agent, or Firm* — Young & Thompson

(57) ABSTRACT

A device for controlled translational displacement of an elongated element that terminates in a frontal functional end, in particular an instrument/tool that is designed to be brought to an internal site in a patient, more particularly an exploratory instrument/surgical tool placed in a catheter or in an operating channel or working channel of a flexible endoscope, whereby the device includes a linear actuator that acts at the rear end of the elongated element that is located opposite its frontal functional end. The device that is characterized in that the actuator includes of a direct-drive electromagnetic linear motor with a shaft that moves in translation relative to a stator and that drives the elongated element, whereby the shaft can also be coupled to a rotary motor.

17 Claims, 7 Drawing Sheets

(51) Int. Cl.
*B21J 15/28* (2006.01)
*A61M 25/09* (2006.01)
*A61B 1/018* (2006.01)
*B31B 1/68* (2006.01)
*A61B 19/00* (2006.01)
*A41H 37/00* (2006.01)

(52) U.S. Cl.
CPC ............... *A41H 37/00* (2013.01); *A61B 17/00* (2013.01); *A61B 19/22* (2013.01); *A61B 19/2203* (2013.01); *A61B 2019/2242* (2013.01); *A61M 2025/09116* (2013.01); *B21J 15/28* (2013.01); *B31B 1/68* (2013.01)

(56) References Cited

U.S. PATENT DOCUMENTS

| | | | | |
|---|---|---|---|---|
| 5,499,632 | A | | 3/1996 | Hill, III et al. |
| 5,632,758 | A | * | 5/1997 | Sklar .............................. 606/170 |
| 6,211,591 | B1 | * | 4/2001 | Kowalski et al. ................ 310/80 |
| 2004/0133075 | A1 | | 7/2004 | Motoki et al. |
| 2004/0152950 | A1 | * | 8/2004 | Kehr .............................. 600/163 |
| 2005/0215983 | A1 | | 9/2005 | Brock |
| 2006/0206006 | A1 | * | 9/2006 | Schara et al. ................. 600/173 |
| 2007/0100201 | A1 | * | 5/2007 | Komiya et al. ................ 600/106 |

\* cited by examiner

DEVICE FOR THE CONTROLLED TRANSLATIONAL DISPLACEMENT OF AN ELONGATE ELEMENT

This invention relates in a general manner to the translational displacement and optionally rotational displacement in two directions of an elongated element, in particular a flexible one, in particular in a pipe or the like, by action at an outside end of said element, in the form of thrust, traction, and torsion.

The controlled or assisted displacement of such elongated elements has become common in the medical field, taking into account the development of exploratory and intervention techniques.

Actually, new so-called mini-invasive approaches in different fields (surgery, gastroenterology, interventional radiology) consist in bringing a flexible instrument in-situ by means of the operating channel of a flexible endoscope or via a catheter.

The flexible instrument is usually actuated manually from the outside under the control of images provided by a visual sensor at the distal end of the endoscope or else also using an external sensor (fluoroscope, ultrasound, . . . ) during operation.

The movements of the flexible instrument are primarily translational movements in the operating channel, rotation of the instrument around its axis (when the friction is not too significant), and actuation of the distal end of the instrument (clamp opening/closing, electric scalpel actuation, plasma torch activation, etc.).

The manual control of the endoscope, sometimes according to several degrees of freedom, simultaneously with the control of the movements of the flexible instrument in the operating channel, requires very high eye-hand coordination, particularly difficult and tiring, even for an experienced practitioner.

There is consequently a need to release the practitioner from certain above-mentioned manipulations or at least to assist him in the execution of the latter.

From the documents US-A-2005/0215983 and "Design of an Endoluminal NOTES Robotic System," Daniel J. Abbott et al., Proceedings of the 2007 IEEE/RSJ, San Diego, Calif., USA, Oct. 29-Nov. 2, 2007, motorized devices for translational displacement of elongated flexible instruments are already known. In these documents, the translational displacement of the instrument that is selected from among an available number of instruments is done by means of a cart that slides on two rails.

This is a bulky mechanical system, subject to wear and tear, requiring a large released space, necessarily mounted on a specific support and not allowing a rotation of the instrument by the practitioner.

From the document EP 1 857 041, a medical instrument in the form of an endoscope or the like whose front end, located in the patient, is provided with a linear actuator that can translationally displace an elongated element is also known.

However, this device requires bringing an electrical supply inside the patient, does not allow a manual manipulation of the elongated element, nor its exchange without total extraction of the endoscope.

From the document EP 1 782 744, an endoscope with an external displacement unit of the instrument that is housed in the tube of the endoscope is finally known.

Nevertheless, the displacement unit has a complex and bulky structure, meaning it cannot be combined with the control handle, and the driving by friction that is implemented is neither precise nor controllable in absolute position.

This invention has as its object to eliminate at least some of the above-mentioned drawbacks.

For this purpose, this invention has as its object a device for controlled translational displacement and optionally rotational displacement, of an elongated element that terminates in a frontal functional end, in particular an instrument or a tool that is designed to be brought to an internal site in a patient, more particularly an exploratory instrument or a surgical tool placed in a catheter or in an operating channel or working channel of a flexible endoscope, whereby said device comprises a linear actuator that acts at the rear end of the elongated element that is located opposite its frontal functional end and outside of the patient, a device characterized in that said actuator consists of a direct-drive electromagnetic linear motor that comprises a shaft that moves in translation relative to a stator and that drives the elongated element, and in that the rear end of the elongated element comprises a portion that makes possible the manual manipulation in translation and/or in rotation of the elongated element.

The invention will be better understood owing to the description below, which relates to preferred embodiments, provided by way of nonlimiting examples, and explained with reference to the accompanying diagrammatic drawings, in which.

Figure 1:
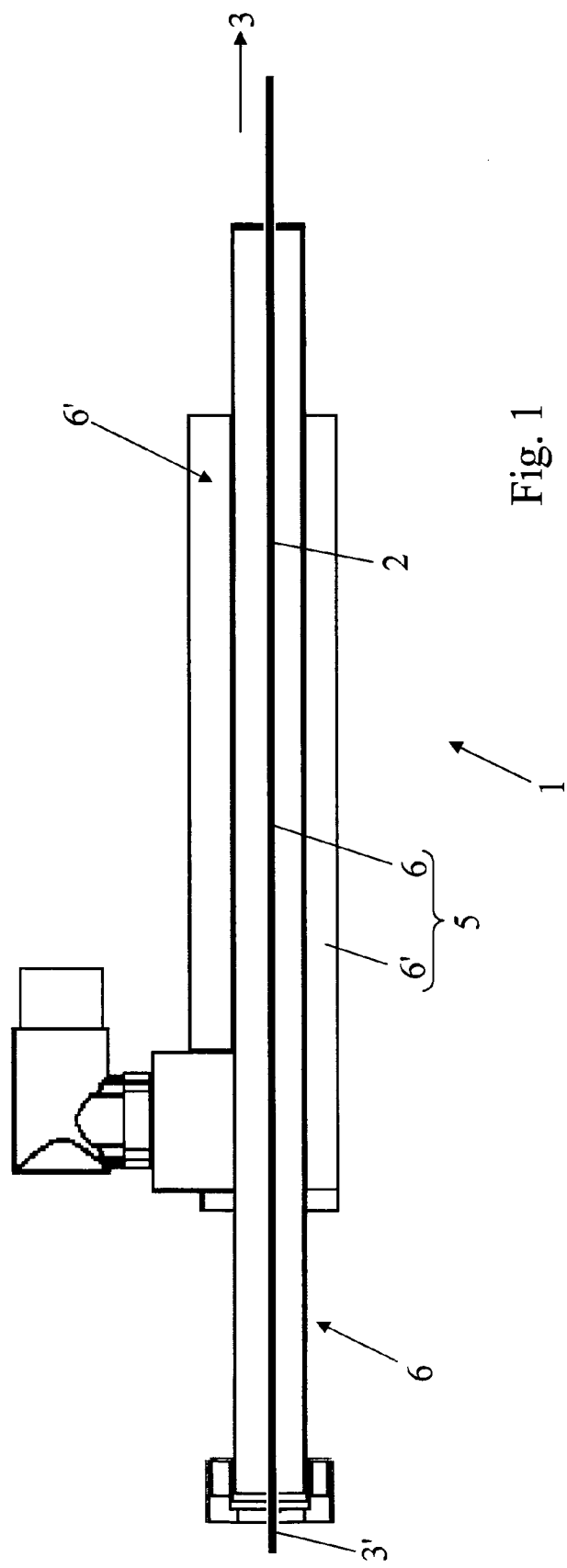
FIG. 1 is a partially transparent diagrammatic representation of a device for controlled translational displacement of an elongated element according to a first embodiment of the invention.
Figure 2:
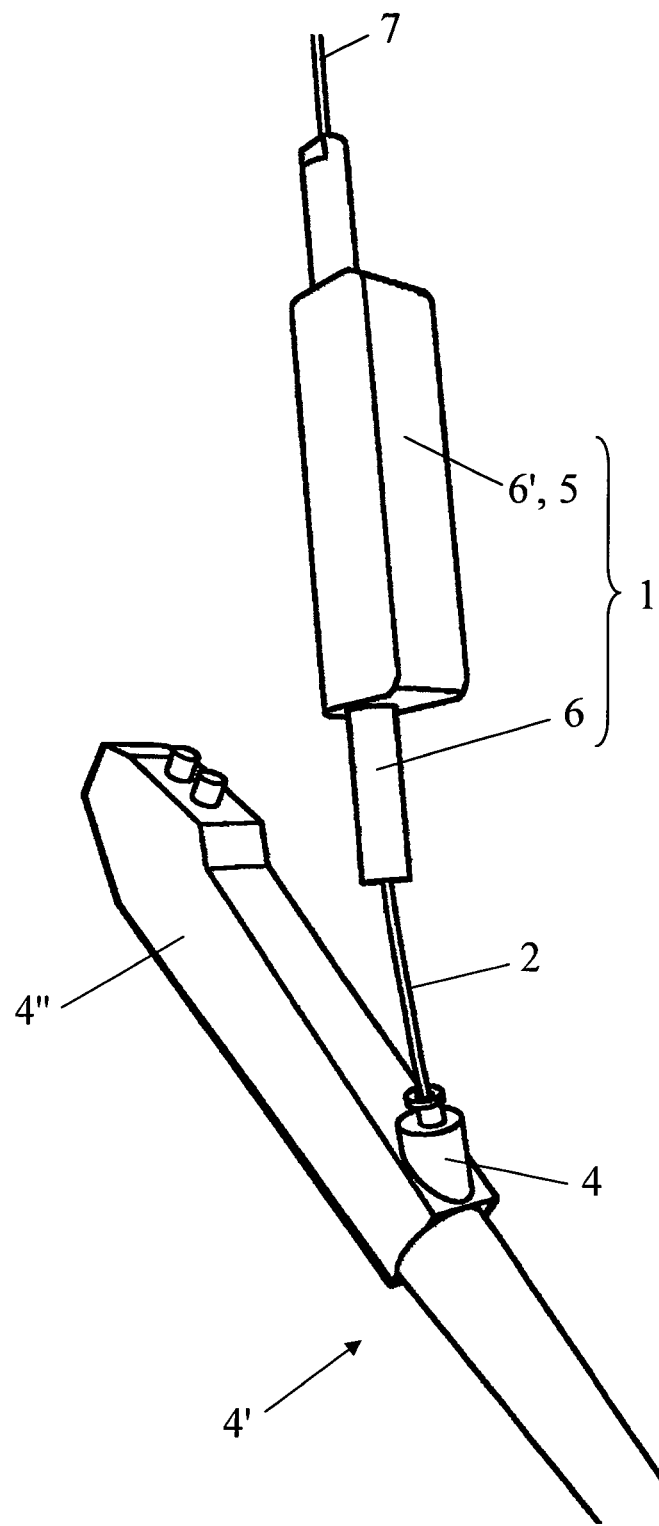
FIG. 2 is a partial perspective view of a flexible endoscope system that comprises a displacement device as shown in FIG. 1.
Figure 3:
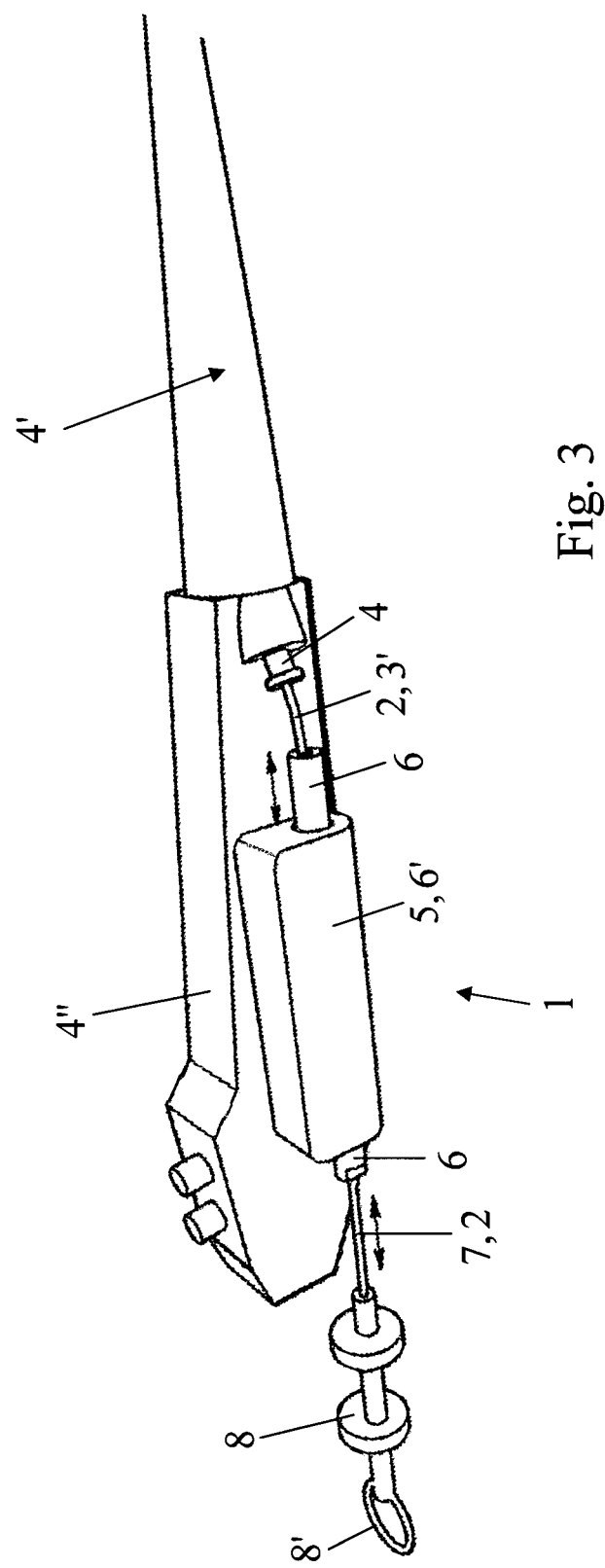
FIG. 3 is a partial perspective view of a variant embodiment of the endoscope system shown in FIG. 2.
Figure 4:
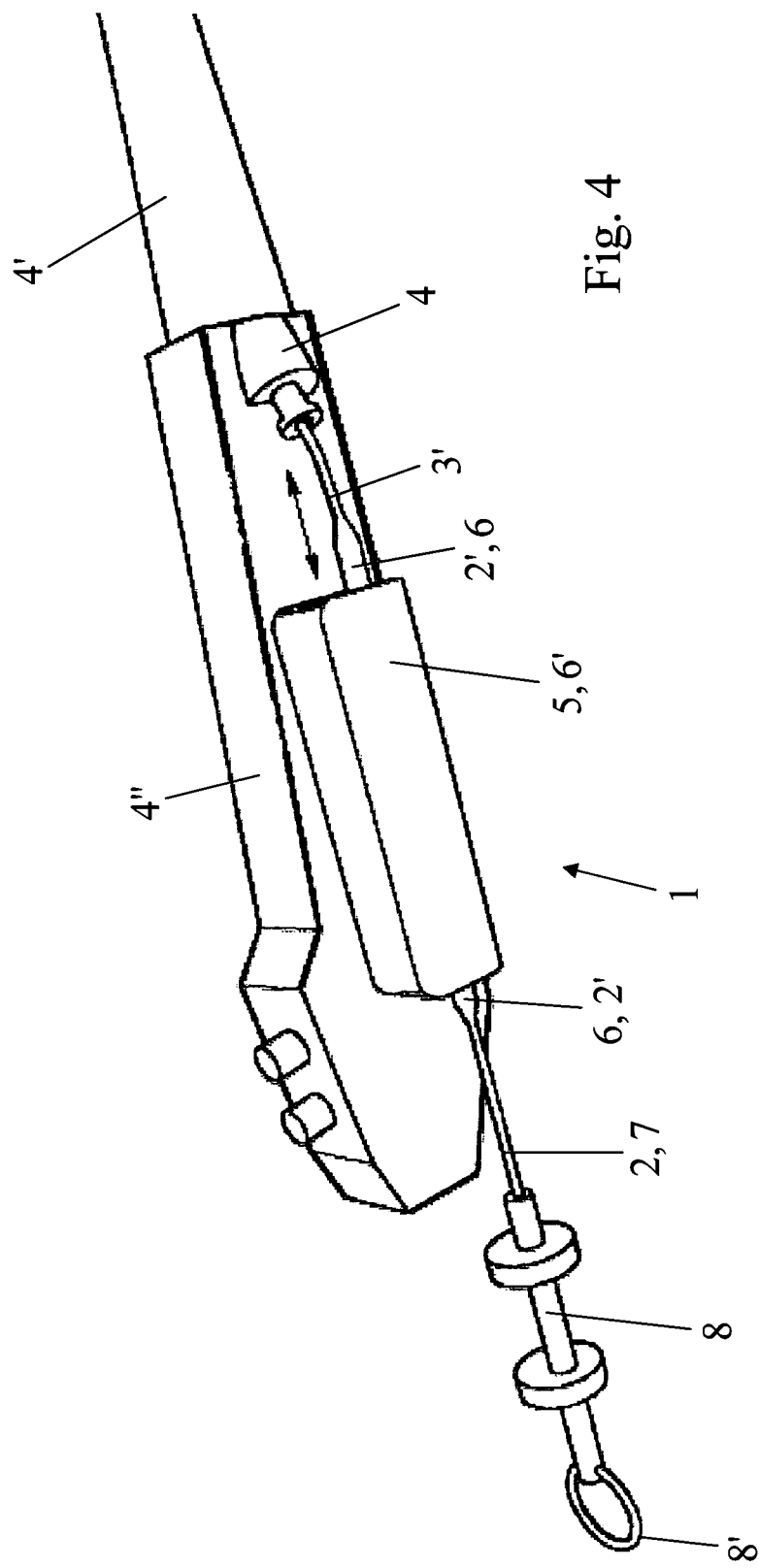
FIG. 4 is a partial view that is similar to FIG. 3 of a flexible endoscope system that comprises a displacement device according to another embodiment of the invention.

FIG. 1, FIGS. 5 to 7, and, partially, FIGS. 2 to 4 show a device 1 for controlled translational displacement and optionally rotational displacement of an elongated element 2 that terminates in a frontal functional end 3, in particular an instrument or a tool that is designed to be brought to an internal site in a patient, more particularly an exploratory instrument or a surgical tool placed in a catheter or in an operating channel or working channel 4 of a flexible endoscope 4', whereby said device comprises a linear actuator 5 that acts at the rear end 3' of the elongated element 2 that is located opposite its frontal functional end 3.

According to the invention, the actuator 5 consists of a direct-drive electromagnetic linear motor that comprises a shaft 6 that can move in translation relative to a stator and that drives the elongated element 2, and the rear end 3' of the elongated element 2 comprises a portion 7 that makes possible the manual manipulation in translation and/or in rotation of the elongated element 2.

Such a linear electrical actuator 5 does not have any part that is subject to wear and tear for the transmission of the movement and does not require any additional part for its functional integration with the elongated element 2. In addition, it has a simple structure and requires little space, makes possible a precise control (and without play), and can easily be combined with or mounted on an element or an existing device (FIGS. 3 and 4).

Preferably, the elongated element 2 extends through the linear motor 5, which greatly facilitates its interchangeability. The integration of the elongated element 2 with the movable part (shaft 6) of the linear motor 5 can have different natures, while advantageously always being direct.

In accordance with a first embodiment of the invention emerging from FIGS. 1, 2 and 3 of the accompanying drawings, the shaft that moves in translation 6 consists of a hollow tube that is provided with permanent magnets and through which the elongated element 2 passes, whereby the latter is made integral by magnetization or by tightening with said tubular movable shaft 6.

The linear motor 5 can then, for example, be of the type that is known under the designation LINMOT (filed name) by the company NTI AG (Switzerland).

The connection by magnetization (between the magnets of the shaft 6 and the elongated element 2 that is at least partially ferromagnetic) has a sufficient force for the transmission without slipping of the traction/thrust movements up to a threshold intensity, while making possible an easy release of the elongated element 2 for the purpose of its replacement and sliding by manual action of said element 2 in said hollow shaft 6.

A connection by mechanical tightening by means of a ring or two opposite rings is also possible relative to the implementation of a hollow shaft 6, optionally in a complementary manner with the magnetic connection, and in particular when the elongated element 2 is made of a non-magnetic or weakly magnetic material (not shown).

This embodiment thus has several advantages, among which in particular the possibility of using existing standard tools and instruments (made of a ferro-magnetic material, or having at least one rear end part made of such a material, when their integration with the shaft is done by magnetization), the possibility of manually changing in a simple manner the instrument and tools 2, and the possibility of joint manipulation or co-manipulation of the tool or the instrument 2 by hand and by the linear motor 5.

Finally, the integration between the shaft 6 and the elongated element 2 is performed over a relatively long length of the latter and not in a localized manner, which promotes the transmission of the thrust or traction force.

In accordance with a second embodiment, shown in FIG. 4 of the accompanying drawings, the shaft 6 that moves in translation consists of a part 2' of the elongated element 2 that has a suitable structure, i.e., integrating a number of permanent magnets in a series. Only the supply of the stator 6' is then necessary.

In an advantageous manner, the rear end portion 7 of the elongated element 2 extends beyond the linear motor 5, if necessary the tubular movable shaft 6, and is preferably provided with at least one element 8, 8' for the manual manipulation of the elongated element 2, optionally in cooperation with the linear motor 5 or in support of or in place of the latter (handle 8, ring 8').

So as to monitor, if necessary, the depth and/or the speed of insertion of the elongated element 2, the device 1 can also comprise a position sensor of the movable shaft 6, combined with or integrated in the linear motor 5, making it possible to measure the actual movement of the elongated element and its effective insertion depth.

According to one enhanced embodiment of the invention, and for the purpose of also being able to provide a movement of the elongated element 2 that is controlled in rotation, the device 1 can also comprise a rotary actuator 9 that can drive the elongated element 2 in rotation in a controlled manner around its longitudinal axis, either directly or by means of the tubular movable shaft 6, whereby the portion 7 of the rear end 3' of the elongated element 2 also extends relative to said rotary actuator 9.

These translative actuators 5 and rotary actuators 9 thus form a controlled external drive unit or module for displacement of the elongated element 2, with two degrees of controlled freedom.

Figure 5:
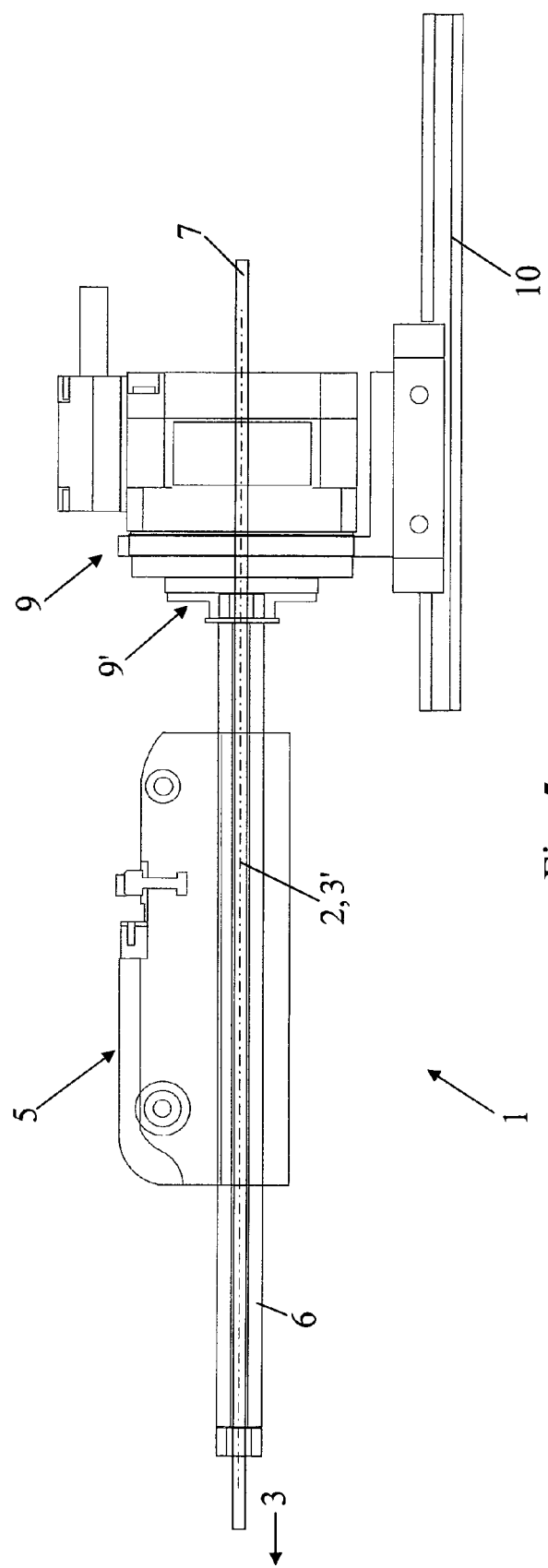
FIGS. 5 to 7 are partially transparent diagrammatic representations of three other embodiments of the invention, allowing a translational and rotational displacement of the elongated element.

According to a first variant embodiment, shown in FIG. 5, the rotary actuator 9 can consist of a motor with a hollow shaft that is mounted in coaxial alignment with the linear actuator 5, mechanically integrated with the latter or with a support 10 that optionally bears this linear actuator 5 and is coupled in rotation with the hollow tube or the part 2' of the elongated element 2 that forms the shaft 6 that moves in translation, whereby the latter is free in rotation at the linear actuator 5.

So as to be able to implement a degraded version of device 1, to be able to change the elongated element 2, or to be able to implement manual maneuvers (switching from motorized operation to manual operation during intervention), it can be provided that the mechanical integration and/or the coupling in rotation of the motor with a hollow shaft 9 is/are detachable in nature.

The support 10 can be provided, for example, with a linear guiding system of the rotary actuator 9, for example aligned with the longitudinal axis of the elongated element 2 that is housed in the linear actuator 5. The rotary actuator 9 is advantageously provided with a connecting piece or coupling piece 9' (mechanical or magnetic) that makes it possible to integrate in rotation the tube 6 or the elongated element 2 with said actuator 9, preferably in a detachable manner.

The motor 9 with a hollow shaft can come, for example, in the form of a motor of the type that is known under the designation "Servo Actuator" from the company Harmonic Drive Systems Inc.

Figure 6:
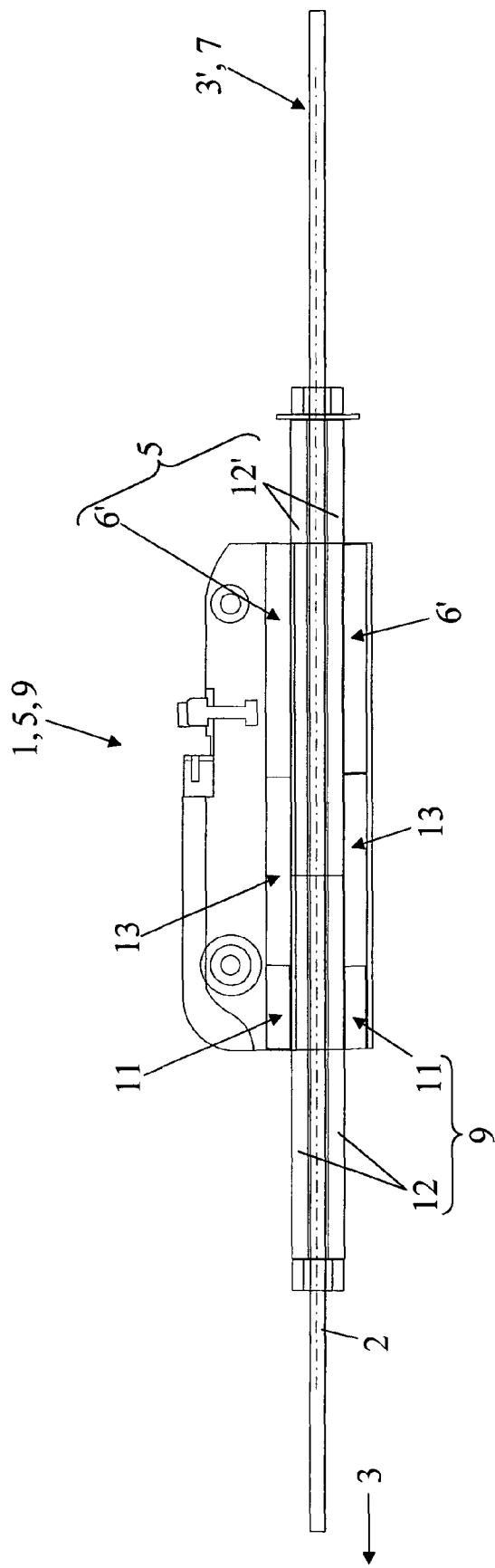

According to a second variant embodiment, and as FIG. 6 of the accompanying drawings shows, the rotary actuator 9 consists of a magnetic motor that is integrated in the linear motor 5, the shaft 6 thus forming a rotor that can be driven in translation and in rotation.

The shaft 6 in tubular form can then be made of two parts, namely a first part 12 that is intended to form the rotor of the rotary actuator 9 and a second part 12' that is intended to form the slide (or sliding rotor) of the linear actuator 5. The displacement device then comprises, at its through passage accommodating the shaft 6, a first stator 6' that is intended to interact with the second part 12' for the purpose of displacement of said shaft 6 in translation and a second stator 11 that is intended to interact with the first part 12 for the purpose of displacement of this shaft 6 in rotation. The two stators being separated axially by a magnetically inactive zone optionally ensuring a guiding function.

Figure 7:
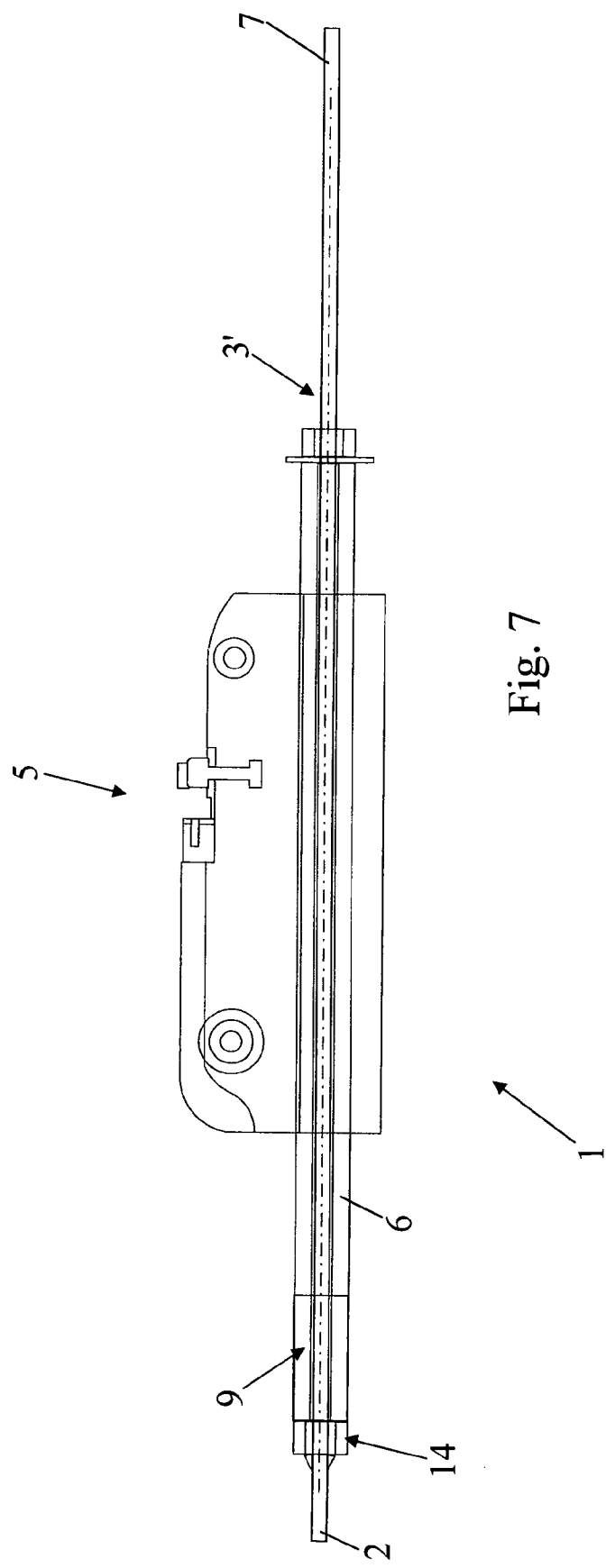

Finally, in accordance with a third variant embodiment, emerging from FIG. 7, the rotary actuator 9 consists of an axial motor that is integrated in the hollow shaft 6 that accommodates the elongated element 2, whereby this axial motor can consist of a motor with a hollow shaft that is small in diameter (able to be integrated in the shaft 6).

The integration in rotation between the motor 9 and the elongated element 2 is obtained by means of a tightening means, for example of the mandrel type, making it possible to couple the motor 9 to the element 2.

Advantageously, the guiding in translation of the hollow shaft 6 that integrates the axial motor with a hollow shaft 9 (for example, a miniaturized version of the motor 9 of the first above-mentioned variant) is performed with locking in rotation in the linear actuator 5.

Finally, it can also be provided that the device 1 comprises or is combined with an automatic or assisted manual control unit, controlling the displacement of the movable shaft 6 by means for controlling the force or speed of the and/or rotary actuator and/or by means for controlling the position. The control of the displacement device 1 can be automatic within the framework of a robotized exploratory or intervention system or can be of the type with assisted manual control, for example, in the form of an electrical control element.

This invention also has as its object, as FIGS. 2 to 4 partially show, an exploratory and/or surgical system, in particular a system with a flexible endoscope 4', comprising at least one instrument or tool 2 in the form of a flexible, elongated element.

This system is characterized in that it also comprises at least one device 1 for controlled translational displacement and optionally rotational displacement as described above, combined with said at least one instrument or tool 2.

The displacement device 1 can constitute a separate module or unit, but it can also be provided that the linear motor 5 is mounted on the—or a—control handle 4" of the system 4', as well as optionally the rotary actuator 9. In this latter case, the linear motor 5 is attached so as not to interfere with the control buttons of the handle 4".

The flexible endoscope system 4' can consist of, for example, a system as described and shown in the patent application PCT No. PCT/FR2008/050312 of Feb. 25, 2008.

Finally, the system can also comprise at least one additional actuator that can control the tool or the instrument that is integrated in the elongated element 2, for example by means of cables, combined with the linear and/or rotary actuator 5, 9.

Of course, the invention is not limited to the embodiments that are described and shown in the accompanying drawings. Modifications are possible, in particular from the standpoint of the structure of the various elements or by substitution of equivalent techniques, without thereby exceeding the scope of protection of the invention.

The invention claimed is:

1. A device for controlled translational displacement, and optionally rotational displacement, of an elongated element that terminates in a frontal functional end, in particular an instrument or a tool that is designed to be brought to an internal site in a patient, more particularly an exploratory instrument or a surgical tool placed in a catheter or in an operating channel or working channel of a flexible endoscope, whereby said device comprises:
    a linear actuator (5) that acts at the rear end of the elongated element (2) that is located opposite the frontal functional end and outside of the patient,
    said actuator (5) comprising a direct-drive electromagnetic linear motor that comprises a tubular movable shaft (6) that moves in translation relative to a stator and that drives the elongated element (2) which extends through the linear motor (5), and
    wherein the rear end (3') of the elongated element (2) comprises a portion (7) that makes possible the manual manipulation in translation and/or in rotation of the elongated element (2),
    wherein the tubular movable shaft (6), forming the rotor of the linear motor (5), consists either of i) a hollow tube provided with permanent magnets and through which magnets the elongated element (2) passes, whereby the elongated element is made integral by magnetization or by tightening with said shaft, or ii) a part (2') of the elongated element (2) integrating a number of permanent magnets in series, and
    wherein the rear end portion (7) of the elongated element (2) extends beyond the linear motor (5), and beyond the tubular movable shaft (6), and is provided with at least one element (8, 8') for direct manual manipulation of the elongated element (2) by a human operator of the device, the direct manual manipulation being by the human operator acting directly on the at least one element (8, 8') for direct manual manipulation of the elongated element (2) by the human operator without power assistance.

2. The device according to claim 1, wherein the shaft (6) that moves in translation comprises a portion (2') of the elongated element (2) that has a suitable structure.

3. The device according to claim 1, further comprising a rotary actuator (9) that can drive in rotation, in a controlled manner, the elongated element (2) around its longitudinal axis, either directly or by means of the tubular movable shaft (6), whereby the portion (7) of the rear end (3') of the elongated element (2) also extends relative to said rotary actuator (9).

4. The device according to claim 3, wherein the rotary actuator (9) comprises a motor with a hollow shaft that is mounted in coaxial alignment with the linear actuator (5), mechanically made integral with the latter or with a support (10) that optionally bears the linear actuator (5) and coupled in rotation with the hollow tube or the portion (2') of the elongated element (2) that forms the movable shaft in translation (6), whereby the latter is free in rotation at the linear actuator (5).

5. The device according to claim 4, wherein the mechanical integration and/or the coupling in rotation of the motor with hollow shaft (9) are detachable in nature.

6. The device according to claim 3, wherein the rotary actuator (9) is a magnetic motor that is integrated in the linear actuator (5), the shaft (6) thus forming a rotor that can be driven in translation and in rotation.

7. The device according to claim 3, wherein the rotary actuator (9) is an axial motor that is integrated in the hollow shaft (6) that accommodates the elongated element (2).

8. The device according to claim 1, further comprising an automatic or assisted manual control unit (4', 4"), controlling the displacement of the movable shaft (6) by means for controlling the force or speed of the linear and/or rotary actuator and/or by means for controlling the position.

9. An exploratory and/or surgical system, in particular a flexible endoscope system, comprising at least one instrument or tool in the form of a flexible elongated element, characterized in that it also comprises at least one device (1) for controlled translational displacement and optionally rotational displacement according to claim 1, combined with said at least one instrument or tool (2).

10. The system according to claim 9, wherein the linear actuator (5) is mounted on a control handle (4") of the system (4') as well as optionally the rotary actuator (9).

11. The system according to claim 9, further comprising at least one additional actuator that can control the tool or the integrated instrument with the elongated element (2).

12. The system according to claim 10, further comprising at least one additional actuator that can control the tool or the integrated instrument with the elongated element (2).

13. The device of claim 1, wherein the at least one element (8, 8') for direct manual manipulation of the elongated element (2) provides the human operator of the device with direct manual translational and rotational movement of the rear end (3') of the elongated element (2) and thereby of the frontal functional end (3) of the elongated element (2).

14. The device of claim 13, wherein the at least one element (8, 8') for direct manual manipulation of the elongated element (2) comprises a handle (8) terminated with a ring (8'), the handle and ring being directly gripped by the human operator to directly and manually manipulate the elongated element (2).

15. The device of claim 1, wherein the at least one element (8, 8') for direct manual manipulation of the elongated element (2) comprises a handle (8) terminated with a ring (8'), the handle and ring being directly gripped by the human operator to directly and manually manipulate the elongated element (2).

16. The device of claim 1, wherein the movable shaft (6), forming the rotor of the linear motor (5), consists of the hollow tube provided with permanent magnets and through which the elongated element (2) passes, whereby the elongated element is made integral by magnetization or by tightening with said shaft.

17. The device of claim 1, wherein the movable shaft (6), forming the rotor of the linear motor (5), consists of a part (2') of the elongated element (2) integrating a number of permanent magnets in series.

\* \* \* \* \*